(12) United States Patent
Spratt et al.

(10) Patent No.: US 10,842,540 B2
(45) Date of Patent: Nov. 24, 2020

(54) METHODS, DEVICES, AND SYSTEMS RELATED TO A SURGICAL DRIVER

(71) Applicant: DePuy Synthes Products, Inc., Raynham, MA (US)

(72) Inventors: Frank Spratt, Middleboro, MA (US); Sheryl Furlan, Lakeville, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 16/178,223

(22) Filed: Nov. 1, 2018

(65) Prior Publication Data

US 2020/0138488 A1 May 7, 2020

(51) Int. Cl.
*A61B 17/70* (2006.01)
*A61F 2/46* (2006.01)
*A61B 17/88* (2006.01)
*A61B 90/00* (2016.01)

(52) U.S. Cl.
CPC ...... *A61B 17/7082* (2013.01); *A61B 17/8886* (2013.01); *A61F 2/4611* (2013.01); *A61B 2090/0811* (2016.02)

(58) Field of Classification Search
CPC ............. A61B 17/7082; A61B 17/8886; A61F 2/4611
See application file for complete search history.

(56) References Cited

U.S. PATENT DOCUMENTS

| | | | |
|---|---|---|---|
| 8,556,937 B2 | 10/2013 | Ludwig et al. | |
| 8,808,307 B2 * | 8/2014 | Robinson | A61B 17/7032 606/104 |
| 9,962,192 B2 | 5/2018 | Hawkins et al. | |

\* cited by examiner

*Primary Examiner* — Christian A Sevilla
(74) *Attorney, Agent, or Firm* — Mintz Levin Cohn Ferris Glovsky and Popeo, P.C.

(57) ABSTRACT

Methods, systems, and devices are provided for the alignment of implants or fastener members. For example, a surgical driver device is provided that has a driver head with a sidewall, a bore extending into a distal end of the driver head that is configured to receive an implant therein, and an alignment post that is disposed within the bore and extends distally beyond a distal opening of the bore. A retention member is disposed along a perimeter of the driver head and is configured to provide an interference fit between the driver head and an implant. A surgical caddie is also provided that has a housing, a plurality of implants on a mounting station, and a removal post that external threads that are matable with internal threads on each of the plurality of implants.

20 Claims, 6 Drawing Sheets

METHODS, DEVICES, AND SYSTEMS RELATED TO A SURGICAL DRIVER

FIELD

The present disclosure relates generally to surgical instruments, methods, and systems for securing surgical implants, and more particularly, to surgical drivers for aligning and driving surgical fastening members.

BACKGROUND

Various fixation devices are commonly used in surgery to align and/or fix a desired relationship between various bone structures within a patient. For example, spinal fixation devices are used in orthopedic surgery to achieve a desired relationship between adjacent vertebral bodies. Such fixation devices typically include one or more spinal fixation elements, such as fixation rods, that can be coupled to adjacent vertebrae by attachment to various bone anchoring devices, such as hooks, bolts, wires, screws, and the like that are embedded in vertebral bodies. In some instances, closure elements, such as screws or nuts, can be used to couple fixation devices to various bone anchoring devices.

However, successful use of these fastening members can be a challenge given their relatively small size and the importance of correctly aligning the fastening members in relation to any driving or implementation components used and the various anchoring devices used. It is common to misalign fastening members and/or strip threads on the fastening members, resulting in operation delay, additional expense, and potential harm to patients.

Thus, there remains a need for surgical instruments, methods, and systems for securing surgical implants.

SUMMARY

Surgical instruments, methods, and systems are provided for securing surgical implants. In a first aspect, a surgical driver device is provided that includes a driver head with a sidewall, a bore that extends into a distal end of the driver head that is configured to receive an implant therein, and an alignment post that is disposed within the bore and extends distally beyond a distal opening of the bore. A retention member is disposed along a portion of a perimeter of the driver head and is also configured to provide an interference fit between the driver head and an implant.

The surgical device can have a number of variations. For example, the implant can be a nut. In another example, the sidewall of the driver head can be discontinuous and a gap can be formed in the sidewall that seats the retention member therein. In still another example, the retention member can be secured to a proximal surface of the gap and can extend distally therefrom. In some embodiments, the retention member can be at least one of a deflectable shaft, a living hinge, and a spring. In another example, the retention member can be a deflectable shaft that has a beveled tip on a distal end thereof. In one embodiment, the retention member can be configured to deflect radially when the driver head receives the implant therein. In another example, the retention member can be configured to move from a neutral position to a securing position when the driver head receives an implant therein, and the retention member can be biased to the neutral position. In one example, the driver head can be formed at a distal end of a driver shaft.

In another aspect, a surgical method is provided that includes aligning a fastening member with a secured article by positioning an alignment post protruding from a driver head into a central opening of the secured article. The method also includes mating inner threads of the fastening member releasably held within the driver head with external threads formed on the secured article. The method further includes the step of removing the driver head such that the fastening member remains threadably secured to the secured article.

The method can have several variations. For example, the secured article can be one of an implanted article and a removal post. The method can also include loading the fastening member onto the driver head in an interference fit. In some examples, the interference fit can be created by an impingement of a retention member associated with the driver head with the fastening member. The method can also include the retention member deflecting radially outward during loading of the fastening member and biasing radially inward after loading. In some embodiments, the implant can be a nut.

In another aspect, a surgical caddie is provided that includes a housing, a plurality of implants disposed within a mounting station, and a removal post that has external threads that are matable with internal threads on each of the plurality of implants.

The caddie can have numerous variations. For example, the mounting station can include a plurality of unthreaded posts that have the plurality of implants positioned thereon. In another example, the plurality of implants can include a plurality of nuts.

BRIEF DESCRIPTION OF THE DRAWINGS

The invention will be more fully understood from the following detailed description taken in conjunction with the accompanying drawings, in which.

Figure 1:
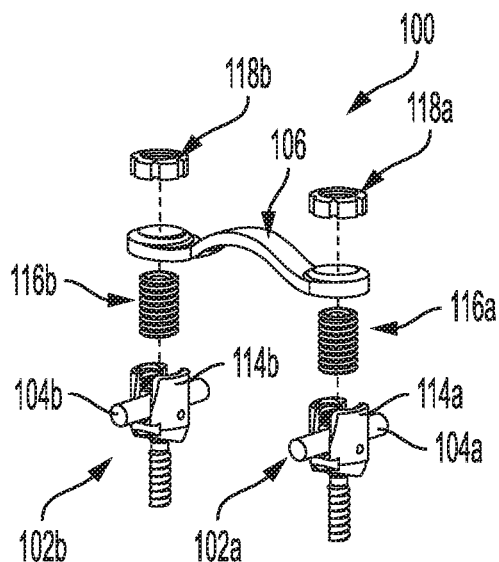
FIG. 1 an exploded perspective view of one embodiment of a spinal fixation system.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

Hereinafter, embodiments of the present disclosure will be described in detail with reference to the accompanying drawings. As those skilled in the art will realize, the described embodiments may be modified in various different ways, all without departing from the spirit or scope of the present disclosure. Further, throughout the specification, like reference numerals refer to like elements.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "coupled" denotes a physical relationship between two components whereby the components are either directly connected to one another or indirectly connected via one or more intermediary components.

Various surgical instruments, methods, and systems for securing surgical implants are provided herein, such as surgical drivers for aligning, loading, and driving surgical fastening members. Spinal fixation devices that are used in orthopedic surgery typically include one or more spinal fixation elements, such as fixation rods, that can be coupled to adjacent vertebrae by as a result of being attached and secured within various anchor assemblies. The anchor assemblies can include hooks, bolts, wires, screws, and the like that can be secured to the spinal fixation elements through the use of various implants, securing means, or fastening members, such as nuts. For example, FIG. 1 illustrates one exemplary embodiment of a spinal fixation system 100 with a connecting plate extending between two bone anchors in the form of bone screws 102a, 102b. The system 100 also has first and second spinal fixation elements in the form of spinal rods 104a, 104b that are connected to the first and second bone anchors 102a, 102b, respectively, and a connecting plate 106 extending between the first and second bone anchors 102a, 102b. The spinal fixation system 100 includes closure mechanisms in the form of first and second set screws 116a, 116b that mate the rods 104a, 104b and the connecting plate 106 to the bone anchors 102a, 102b. The set screws 116a, 116b are threadably engaged in a rod receiving portion 114a, 114b of each bone anchor 102a, 102b to mate the spinal fixation rods 104a, 104b to the bone anchors 102a, 102b, and first and second nuts 118a, 118b threadably engage the set screws 116a, 116b to fix the connecting plate 106 to the rod-receiving portion 114a, 114b of each bone anchor 102a, 102b.

Figure 2:
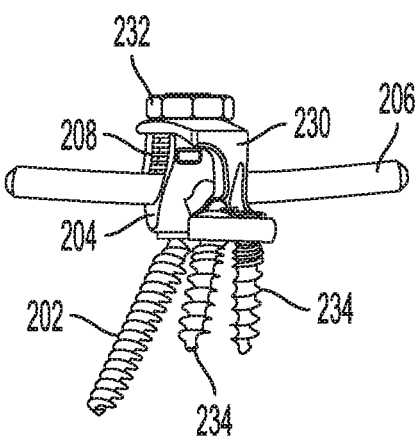
FIG. 2 is a perspective view of a bone anchor assembly and a spinal rod.
Figure 3:
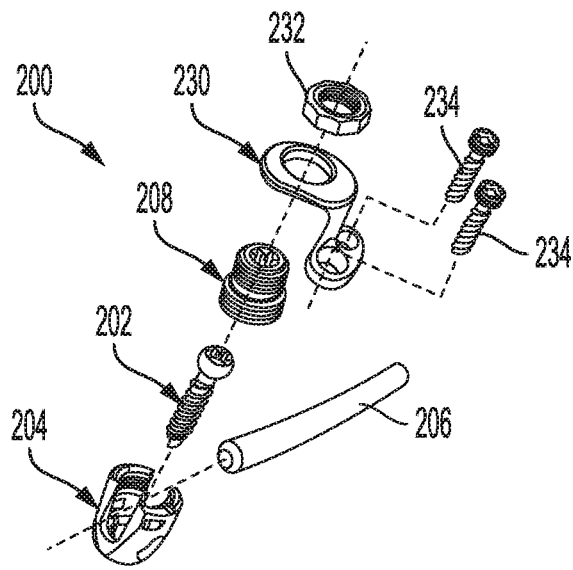
FIG. 3 is a perspective exploded view of the bone anchor assembly and spinal rod of FIG. 2.
Figure 4:
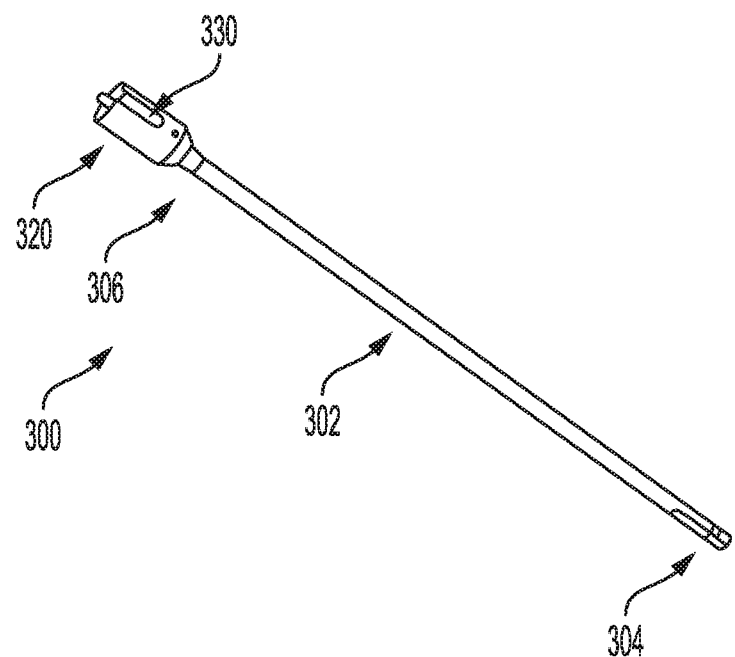
FIG. 4 is a perspective view of one embodiment of a driver.
Figure 5:
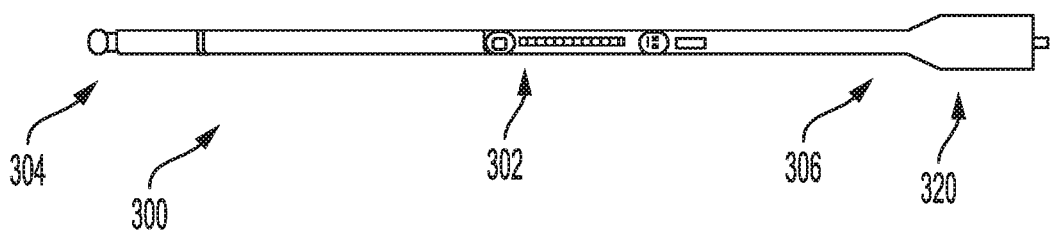
FIG. 5 is a perspective view of the driver of FIG. 4.
Figure 6:
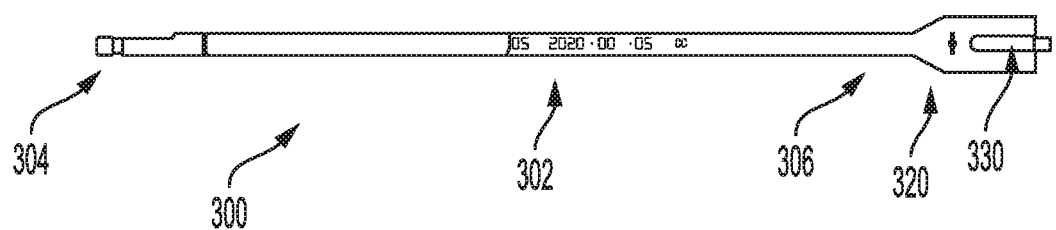
FIG. 6 is a perspective view of the driver of FIG. 4.

FIGS. 2 and 3 illustrate another exemplary bone anchor assembly 200 with a spinal rod 206. The bone anchor assembly 200 includes a bone anchor 202, a receiver member 204, a closure mechanism in the form of a set screw 208, a bracket or wing 230, a nut 232, and one or more auxiliary bone anchors 234. In use, the wing 230 can be secured to the receiver member 204, e.g., using the closure mechanism 208 and nut 232, thereby providing the ability to augment fixation of the bone anchor 202 with the one or more auxiliary bone anchors 234. Additional examples of spinal fixation devices can be found in, for example, U.S. Pat. No. 8,556,937, filed on May 14, 2012, and U.S. Pat. No. 9,962,192, filed on Mar. 17, 2016, both of which are incorporated herein by reference in their entirety.

While various implants or fastening members, such as nuts 118a, 118b, 232, can be threaded onto various closure mechanisms, such as set screws 116a, 116b, 208, it can be challenging to correctly align and load the implants within drivers for deployment. It can be equally challenging to correctly place the implants on closure mechanisms during a surgical procedure given the small size of the implants and the fine maneuvering required during surgery. Likewise, it can be equally difficult to subsequently remove the implants from the drivers without deployment within a patient's body if, for some reason, a surgeon decides not to deploy a particular implant after it is loaded with a driver. Thus, provided herein is a surgical driver device that assists in reliable and successful alignment of implants as well as the subsequent removal of such implants.

An exemplary surgical driver device has a driver head that has a sidewall and a bore that extends into a distal end of the driver head and that is configured to receive an implant therein. An alignment post is disposed within the bore and extends distally beyond a distal opening of the bore. The surgical driver device can also have a retention member disposed along a perimeter of the driver head, and the retention member can be configured to provide an interference fit between the driver head and an implant. The retention member is useful to enable the implant to be reliably held in place within the driver device regardless of the orientation of the driver device.

FIGS. 4-8 illustrate one embodiment of a surgical driver device 300. The driver device 300 has an elongate shaft 302 with a driver head 320 on a distal end 306 thereof. The driver head has a bore 322 extending into a distal end of the driver head 320, an alignment post 324 extending distally from the bore 322, and a retention member 326 disposed along a perimeter of the driver head 320. The elongate shaft 302 has a proximal end 304 and the distal end 306, and the proximal end 304 of the shaft 302 can be operably coupled to a variety of mechanisms that actuate the driver device, including manual handles, surgical robotic systems, etc., by rotating the driver device 300.

The driver head 320 has a sidewall defining the outer surface thereof, and an opening or gap 330 is formed in the sidewall thereof. The gap 330 extends from a distal edge of the sidewall of the driver head 320 to a proximal point thereon, and the gap 330 can have a variety of shapes, including a U-shape, a rectangular shape, an oval shape, or the like. For example, the gap 330 illustrated in FIG. 8 has a general U-shape.

As noted above, the bore 322 extends into the driver head from a distal end thereof. The bore is in the form of an opening or space that is configured to receive and engage an implant or fastening member therein, such as a nut. The bore opening can be of any shape that is suitable to engage an implant or fastening member such that the implant or fastening member can be rotatably driven by the driver device 300. For example, the bore opening can be hexagonal, octagonal, or of any other shape that is complementary to that of the implant or fastening member.

The bore 322 can be formed in a variety of ways. In one embodiment the bore 322 is machined out of a solid piece of material that makes up the driver head 320. However, the bore 322 can alternatively be formed as a result of forming the driver head 320 out of a flat piece of material that is subsequently formed into a desired shape.

Figure 7:
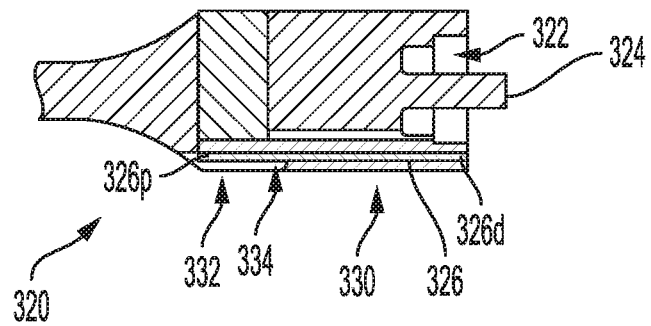
FIG. 7 is a cross-sectional view of a head of the driver of FIG. 4.

The alignment post 324 is centrally disposed within the bore 322 and extends distally beyond the distal opening of the bore 322, for example as illustrated in FIG. 7. The alignment post 324 can protrude from the distal end of the bore 322 by any amount that is suitable for use in a given surgical procedure. Further, the alignment post 324 can have a variety of shapes, but in the illustrated embodiment the alignment post 324 is in the shape of a solid cylinder that is configured to be received within various spinal fixation devices. The alignment post 324 is configured to properly align the driver head 320 of the surgical driver device 300 during loading of an implant and during subsequent removal of the implant, either from deploying the implant onto a spinal fixation device or removing the implant without deployment. Properly aligning the driver head 320 through use of the alignment post 324 allows for the implant itself to be properly aligned during loading and removal.

The illustrated alignment post 324 can be formed in a variety of ways. In one embodiment the alignment post 324 can be formed during the process of machining the bore 322 out of the driver head 320 such that the alignment post 324 remains centrally positioned within the bore. In other embodiments the alignment post 324 can be formed by securing a post to the driver head 320 inside of the bore 322 through various techniques known in the art such as through the use of adhesives, welding, and of friction fit the post within a smaller bore, etc.

The retention member 326 is disposed along the perimeter of the driver head 320, and it is configured to provide an interference fit between the driver head 320 and an implant or fastening member that is disposed within the driver head 320. The retention member 326 can take a variety of forms, such as a deflectable shaft, a living hinge, a spring, various compression members, etc. In one embodiment the retention member 326 is in the form of an elongate shaft that is disposed in the gap 330 that is formed in the sidewall of the driver head 320. A proximal end 326p of the retention member 3626 is fixed to a proximal surface of the gap 330, and the retention member 326 extends distally therefrom.

Figure 8:
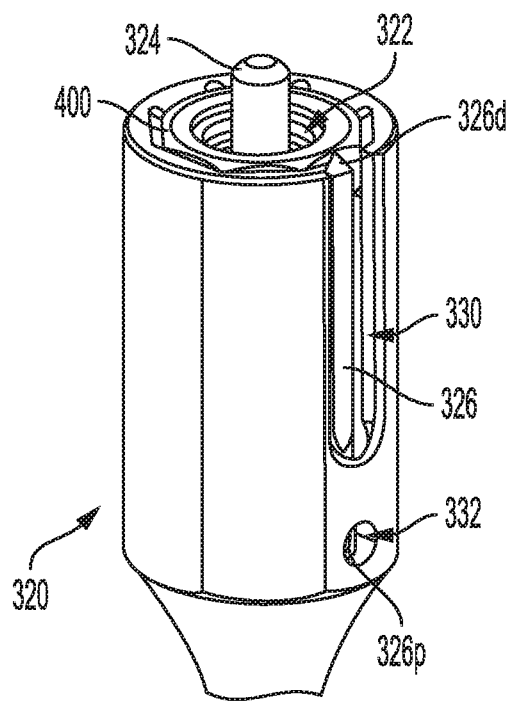
FIG. 8 is a perspective view of the head of the driver of FIG. 4.
Figure 9:
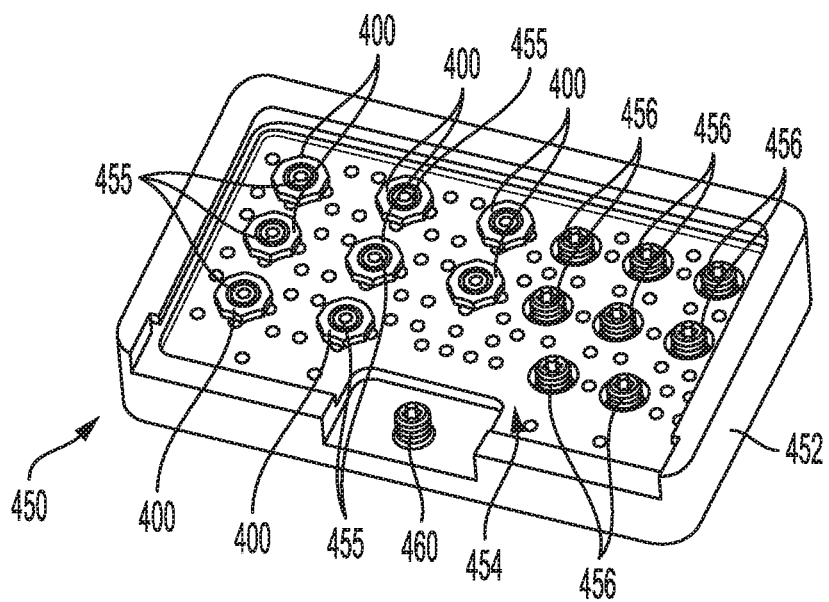
FIG. 9 is a perspective view of a surgical caddie with various surgical implants thereon.
Figure 10:
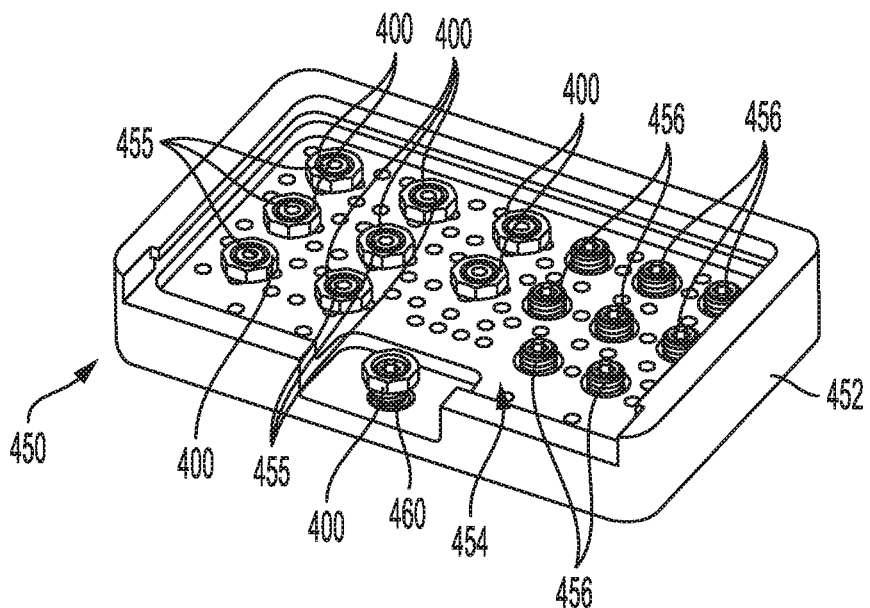
FIG. 10 is a perspective view of the surgical caddie of FIG. 9.

The retention member 326 extends distally in the same direction as the alignment post 324. In a neutral position, before an implant is loaded within the driver device, the retention member 326 generally extends into the volume of the bore by a distance that is effective to somewhat occlude the bore. Upon loading an implant within the bore 322 of the driver head 320, the retention member 326 is configured to deflect such that it flexes or bends radially outward under contact with the implant, thus exerting a force on the implant that creates an interference fit of the implant within the bore of the driver. The magnitude of the force and the interference fit is sufficient to enable an implant to be held within the bore of the driver regardless of the orientation of the driver device. Once an implant is removed from the driver device 300, such as through deployment, the retention member 326 is configured to return to its neutral or starting position. Thus, as illustrated in FIG. 8, the retention member 326 is spring biased to sit in contact with the implant when the implant is loaded, thus acting to hold the implant in place when loaded. In one embodiment the retention member has a distal end 326d that is beveled such that, when the driver head 320 is pressed onto an implant to load the implant therein, the beveled distal end 326d contacts an edge of the implant and is forced radially outward, causing the retention member 326 as a whole to flex or bend radially outward to receive the implant in the bore 322 while maintaining contact with the implant.

The retention member 326 can be attached to the sidewall of the driver head 320 in a variety of different ways, such as through the use of adhesives, welding, interference fit, or the like. For example, the retention member 326 can be welded at the proximal end 326p thereof to the driver head 320 through a small opening 332 in the sidewall of the driver head 320 that is proximal to the gap 330. A small bore 334 connects the openings 330, 332 and extends parallel to the elongate shaft 302 of the driver device 300. During manufacture, the elongate shaft of the retention member 326 can be inserted proximally into the opening 330, through the small bore 334, and seated against proximal driver head material in the opening 332. The proximal end 326p of the retention member 326 is then welded to the driver head 320 through the opening 332.

The driver head 320, the alignment post 324, and the retention member 326 can be made of a variety of materials, such as medical grade metals and plastics, including those that are suitable for sterilization and reuse. The retention member 326 can be made of various metals and plastics, such as spring steel. The driver head 320, the alignment post 324, and the retention member 326 can each be made of the same materials or separate materials, for example making the driver head 320 and the alignment post 324 of a more rigid material while making the retention member 326 of a more flexible material. The driver device 300 and the driver head 320 can have a variety of sizes, and one skilled in the art can determine appropriate dimensions based on a desired use of the device driver 300.

As mentioned above, the surgical driver device is configured to receive an implant therein. For example, FIGS. 8-13 illustrate one embodiment of an implant or fastening member 400 in the form of a nut that can be held on a surgical caddie 450 until it is ready for use in a surgical procedure. As illustrated, the implant 400 is a nut with an octagonal outer surface that is configured to be engaged by the retention member 326. The implant 400 also includes a bore or opening therethrough with a threaded inner surface wherein the threads are configured to engage outer threads on various spinal fixation devices, such as outer threads on the set screws 116a, 116b, 208 and other similar set screws.

As noted, a surgical caddie 450, as illustrated in FIGS. 9-13, can house a plurality of implants 400 until such time that they are ready to be used in a procedure. The caddie 450 has a housing 452 with a flat, rectangular mounting station 454 for implants 400 and set screws 456 similar to the set screws 116a, 116b, 208 discussed above. The plurality of implants 400 are aligned on a corresponding plurality of unthreaded posts 455 until they are ready for use. The posts 455 have a generally hollow cylindrical shape with a central bore that is configured to receive the alignment post 324 of the driver head 320 to assist in alignment during loading of the corresponding implant 400. The caddie also includes a number of set screws 456 that are aligned in recesses in the mounting station 454. A removal post 460 extends from a surface of the housing 452 and can be separate from a surface of the mounting station 454.

The removal post 460 can be permanently coupled to the housing 452, and it has a generally hollow cylindrical shape with a central opening that is configured to receive the alignment post 324 of the driver head 320 therein to assist with alignment of the surgical driver device 300 when removing a loaded implant 400, as discussed below. External threads extend around an outer surface of the removal post 460, and the threads are configured to mate with the internal threads on each of the plurality of implants 400. The housing 452 can have one or more openings therein to assist with cleaning the caddie 450, and a variety of covers can be placed over the caddie 450 prior to and after use.

The implants 400, the surgical caddie 450, and the set screws 456 can be made of a variety of materials, such as medical grade metals and plastics, including those that are suitable for sterilization and reuse. The implants 400, the surgical caddie 450, and the set screws 456 can have a variety of sizes, and one skilled in the art can determine appropriate dimensions based on a desired use.

Figure 11:
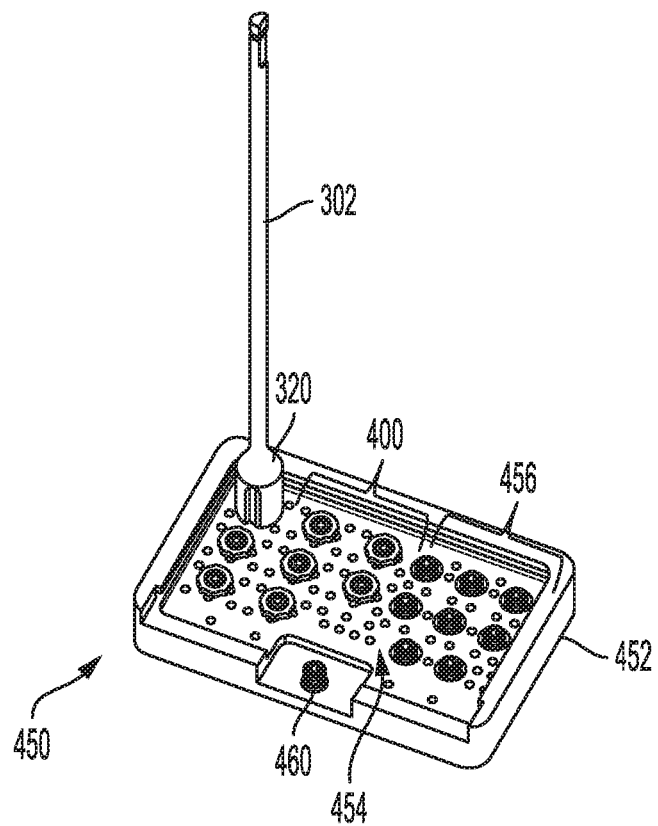
FIG. 11 is a perspective view of the driver of FIG. 4 with the surgical caddie of FIG. 9.
Figure 12:
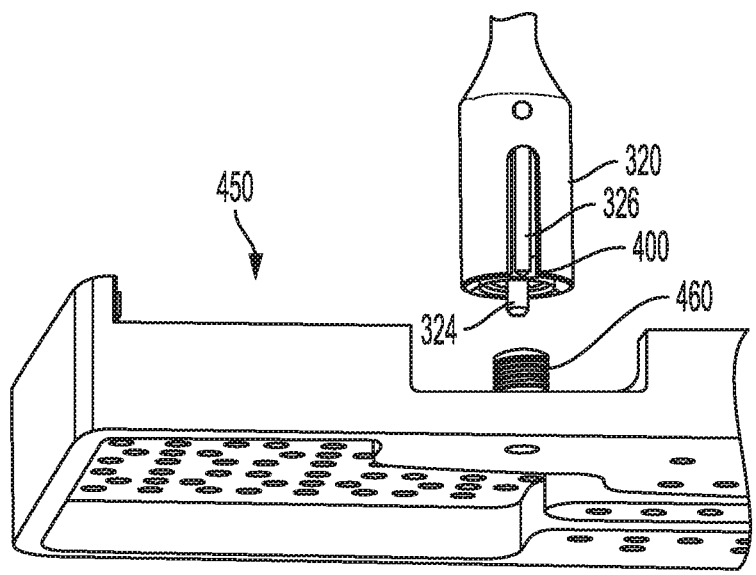
FIG. 12 is a perspective view of the head of the driver of FIG. 4 with the surgical caddie of FIG. 9.
Figure 13:
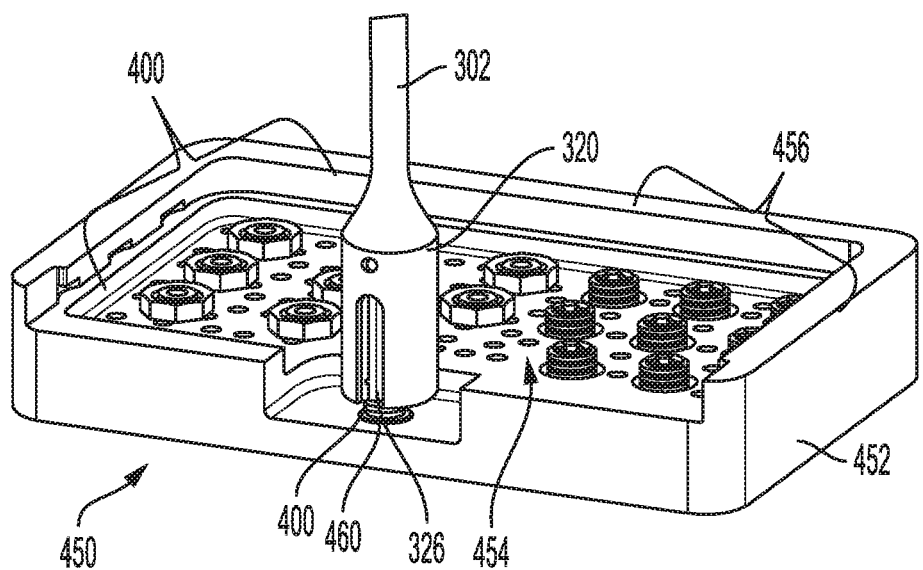
FIG. 13 is a perspective view of the head of the driver of FIG. 4 with the surgical caddie of FIG. 9.

The driver device and system described herein can be used in the following manner First, an implant 400 is loaded onto the surgical driver device 300 by maneuvering the driver device 300 such that the driver head 320 is positioned over one of the implants 400 on the caddie 450. As discussed above, this movement can be accomplished in a variety of ways, such as by attaching the device 300 to a manual handle and maneuvering by hand or attaching the device 300 to a robotic system. Once the driver is properly positioned, the alignment post 324 is inserted into the corresponding unthreaded post 455 on the caddie 450 to ensure proper alignment, and the driver head 320 is pressed down over the selected implant 400, as illustrated in FIG. 11. As the driver head 320 is pressed down, the implant 400 is received within the driver head 320 and the retention member 326 deflects radially outward, causing the retention member 326 to allow the implant 400 to be received into the bore 322 of the head 320. After the implant 400 is received therein, the retention member 326, which is biased radially inwardly, exerts a force on the implant and causes the implant to reside within the head 320 in an interference fit.

To deploy an implant 400 in a body of a patient, the driver head 320 is aligned over a secured article within a patient, such as the various spinal fixation devices discussed above. The alignment post 324 is first inserted into a central opening of the secured article to ensure alignment. The inner threads of the implant 400 are then mated with external threads on the secured article, and the driver device 300 is rotated to thread the implant 400 onto the secured article. Once the implant 400 is threaded thereon, the driver head 320 can be removed, causing the retention member 326 to deflect radially outward again and release the implant from the driver head 320 while the implant remains secured to the secured article.

After an implant 400 is loaded, a surgeon might wish to remove the implant 400 from the driver head for a variety of reasons without actually deploying the implant 400 in a body of a patient. Thus, to remove an implant 400 without deployment, a similar approach is used to that of deploying an implant 400 in a body. However, instead of aligning the driver head 320 over a secured article within a patient, the driver head 320 is aligned over the removal post 460. The alignment post 324 is inserted into the opening of the removal post 460 to ensure alignment, and the inner threads of the implant 400 are mated with the external threads on the removal post 460. The driver device 300 is then rotated to thread the implant 400 onto the removal post 460. Once the implant 400 is threaded thereon, the driver head 320 can be removed, causing the retention member 326 to deflect radially outward again and allow the implant 400 to be released from the driver head 320 and remain secured to the removal post 460.

While there have been shown and described illustrative embodiments, it is to be understood that various other adaptations and modifications may be made within the spirit and scope of the embodiments herein. Thus, the embodiments of the present disclosure may be modified in any suitable manner in accordance with the scope of the present claims.

The foregoing description has been directed to embodiments of the present disclosure. It will be apparent, however, that other variations and modifications may be made to the described embodiments, with the attainment of some or all of their advantages. Accordingly, this description is to be taken only by way of example and not to otherwise limit the scope of the embodiments herein.

What is claimed is:

1. A surgical driver device, comprising:
a driver head having a sidewall;
a bore extending into a distal end of the driver head and being configured to receive an implant therein;
an alignment post disposed within the bore and extending distally beyond a distal opening of the bore; and
a retention member disposed along a portion of a perimeter of the driver head and configured to provide an interference fit between the driver head and an implant;
wherein the sidewall of the driver head is configured to provide rotational force to an implant received in the bore.

2. The device of claim 1, wherein the implant is a nut.

3. The device of claim 1, wherein the sidewall is discontinuous and a gap formed in the sidewall seats the retention member therein.

4. The device of claim 3, wherein the retention member is secured to a proximal surface of the gap and extends distally therefrom.

5. The device of claim 1, wherein the retention member is at least one of a deflectable shaft, a living hinge, and a spring.

6. The device of claim 1, wherein the retention member is a deflectable shaft having a beveled tip on a distal end thereof.

7. The device of claim 1, wherein the retention member is configured to deflect radially when the driver head receives the implant therein.

8. The device of claim 1, wherein the retention member is configured to move from a neutral position to a securing position when the driver head receives an implant therein, and the retention member is biased to the neutral position.

9. The device of claim 1, wherein the driver head is formed at a distal end of a driver shaft.

10. The device of claim 1, wherein the bore forms inward facing polygonal surfaces of the sidewall of the driver head, and the inward facing polygonal surfaces of the sidewall are configured to provide rotational force to an implant received in the bore.

11. The device of claim 10, wherein the inward facing polygonal surfaces of the sidewall have a hexagonal or octagonal cross section.

12. The device of claim 1, wherein the retention member has a first Young's modulus and the driver head has a second Young's modulus, and the first Young's modulus is less than the second Young's modulus.

13. The device of claim 1, wherein the retention member is configured to deflect through a gap formed in the sidewall when the driver head receives an implant therein.

14. The device of claim 1, wherein a distal end of the retention member extends into the bore.

15. The device of claim 1, wherein the alignment post is configured to provide no rotational force to an implant received within the driver head.

16. A surgical driver device, comprising:
a driver head having a sidewall;
an implant cavity extending into a distal end of the driver head, the implant cavity having a polygonal cross section, the implant cavity being configured to receive and transmit a drive force to an implant therein;
an alignment post disposed within the implant cavity and extending distally beyond the distal end of the driver head; and
a retention member disposed along a portion of a perimeter of the driver head and configured to provide an interference fit between the driver head and an implant.

17. The device of claim 16, further comprising at least one gap formed in the sidewall, wherein the retention member extends distally from the gap.

18. The device of claim 16, further comprising only a single gap formed in the sidewall, wherein the retention member extends distally from the gap.

19. The device of claim 16, wherein the alignment post is cylindrical.

20. The device of claim 16, wherein the retention member is distinct from the driver head.

\* \* \* \* \*